(12) United States Patent
Hendrix et al.

(10) Patent No.: US 12,188,941 B2
(45) Date of Patent: Jan. 7, 2025

(54) USE OF BACTERIAL EXTRACELLULAR VESICLES AS A BIOMARKER FOR INTESTINAL BARRIER PERMEABILITY AND MICROBIAL DYSBIOSIS

(71) Applicant: Universiteit Gent, Ghent (BE)

(72) Inventors: An Hendrix, Heusden (BE); Olivier De Wever, Heusden (BE); Joeri Tulkens, Ledeberg (BE)

(73) Assignee: Universiteit Gent, Ghent (BE)

(*) Notice: Subject to any disclaimer, the term of this patent is extended or adjusted under 35 U.S.C. 154(b) by 898 days.

(21) Appl. No.: 17/295,383

(22) PCT Filed: Nov. 21, 2019

(86) PCT No.: PCT/EP2019/082054
§ 371 (c)(1),
(2) Date: May 19, 2021

(87) PCT Pub. No.: WO2020/104577
PCT Pub. Date: May 28, 2020

(65) Prior Publication Data
US 2022/0003775 A1    Jan. 6, 2022

(30) Foreign Application Priority Data
Nov. 22, 2018  (EP) .................................. 18207847

(51) Int. Cl.
*G01N 33/92*  (2006.01)
*G01N 33/68*  (2006.01)

(52) U.S. Cl.
CPC .......... *G01N 33/6827* (2013.01); *G01N 33/92* (2013.01); *G01N 2400/50* (2013.01); *G01N 2800/06* (2013.01)

(58) Field of Classification Search
CPC ............... G01N 33/6827; G01N 33/92; G01N 2400/50; C12Q 1/04
See application file for complete search history.

(56) References Cited

FOREIGN PATENT DOCUMENTS

WO    2017/053544 A1    3/2017

OTHER PUBLICATIONS

Konoshenko, M et al. Isolation of extracellular vesicles: general methodologies and latest trends. Jan. 2018. BioMed Research international, vol. 2018, 1-28 (Year: 2018).*
Guo, S et al Lipopolysaccharide causes an increase in intestinal tight junction permeability in vitro and in vivo by inducing enterocyet membrane expression and localization of TLR-4 and CD-14. Feb 2103, Am J. Path, V 182, 375-387. (Year: 2013).*
(Continued)

*Primary Examiner* — Samuel C Woolwine
*Assistant Examiner* — Lisa Horth
(74) *Attorney, Agent, or Firm* — TraskBritt

(57) ABSTRACT

The present disclosure relates to a method of analyzing a biofluid of a subject for the presence of bacterial extracellular vesicles (EV), the method comprising the steps of a) extracting bacterial EV from the biofluid, b) analyzing the bacterial EV-extracted molecular patterns for the presence of a disease marker, wherein the disease marker is a disease-specific molecular pattern of the subject; and the subject comprising patients diagnosed with HIV, IBD or cancer or the subject receiving a treatment.

18 Claims, 10 Drawing Sheets

(56) References Cited

OTHER PUBLICATIONS

Park, K-S et al Sepsis-like systemic inflammation induced by nano-sized extracellular vesicles from feces. Front in Mich, Aug. 2018, V9, p. 1-11. (Year: 2018).*
Sork, et al. Heterogeneity and interplay of the extracellular vesicle small RNA transcriptome and proteome. Jul. 2018. Sci Reports, 8, 1-10. (Year: 2018).*
Yoo, JY et al.16S rRNA gene-based metagenomic analysis reveals differences in bacteria-derived extracellular vesicles in the urine of pregnant and non-pregnant women. 2016. Experimental & Molec Medicine, 48, e208 (Year: 2016).*
Zhang, X. et al. Metaproteomics reveals associations between microbiome and intestinal extracellular vesicle proteins in pediatric inflammatory bowel disease. Jul. 20, 2018. Nat Comm 9: 1-14. (Year: 2018).*
Buurman et al. Population pharmacokinetics of infliximab in patients with inflammatory bowel disease: potential implications for dosing in clinical practice. 2015.Aliment Pharmacol Ther. 42:529-539. (Year: 2015).*
Derikx et al., "Non-Invasive Markers of Gut Wall Integrity in Health and Disease," World J. Gastroenterol, vol. 16, No. 42, (2010), pp. 5272-5279.
Ellis et al., "Virulence and Immunomodulatory Roles of Bacterial Outer Membrane Vesicles," Microbiology and Mol. Biol. Rev., (2010), pp. 81-94.
Guo et al., "Lipopolysaccharide Causes an Increase in Intestinal Tight Junction Permeability in Vitro and in Vivo by Inducing Enterocyte Membrane Expression and Localization of TLR-4 and CD14," The Am. J. Pathol., vol. 182, No. 2, (Feb. 2013), pp. 375-387.
International Search Report for International Application No. PCT/EP2019/082054, mailed Apr. 2, 2020, 6 pages.
International Written Opinion for International Application No. PCT/EP19/082054, mailed Apr. 2, 2020, 10 pages.
Serino, "Molecular Paths Linking Metabolic Diseases, Gut Microbiota Dysbiosis and Enterobacteria Infections," j. Mol. Biol., vol. 430, Issue 5, (Mar. 2018), pp. 581-590.
Tulkens et al., "Increased Levels of Systemic LPS-Positive Bacterial Extracellular Vesicles in Patients with Intestinal Barrier Dysfunction," Gut, vol. 69, No. 1, (Dec. 2018), pp. 191-193.
Barros et al., "Quantitative lipopolysaccharide analysis using HPLC/MS/MS and its combination with the limulus amebocyte lysate assay," Journal of Lipid Research, vol. 56, (2015), pp. 1363-1369.
Cani et al., "Human Gut Microbiome: Hopes, Threats and Promises," Cani PD. Gut, (2018), pp. 1-10.
Cohen et al., Natural Human Antibodies to Gram-Negative Bacteria: Immunoglobulins G, A, and M, Source: Science, vol. 152, No. 3726, (May 27, 1966), pp. 1257-1259.
Deun et al., "The Impact of Disparate Isolation Methods for Extracellular Vesicles on Downstream RNA Profiling," Journal of Extracellular Vesicles, vol. 3:24858, (2014), 15 pages.
Grander et al., Recovery of Ethanol-Induced Akkermansia Muciniphila Depletion Ameliorates Alcoholic Liver Disease, Gut, (2017), pp. 1-11.
Hanninen et al., "Akkermansia Muciniphila Induces Gut Microbiota Remodelling and Controls Islet Autoimmunity in NOD Mice," Gut, vol. 67, (2018), pp. 1445-1453.
Hubatsch et al., "Determination of Drug Permeability and Prediction of Drug Absorption in Caco-2 Monolayers," Nat. Protocol, vol. 2, No. 9, (2007), pp. 2111-2119.
Increased Human Intestinal Barrier Permeability Plasma Biomarkers Zonulin and FABP2 Correlated With Plasma LPS and Altered Gut Microbiome in Anxiety or Depression, Gut, vol. 67, No. 8, (Aug. 2018), pp. 1555-1557.
Kuek et al., "Immune-Mediated Inflammatory Diseases (IMIDs) and Biologic Therapy: a Medical Revolution," Postgrad Med. J., vol. 83, (2007), pp. 251-260.
Neto et al., "Chapter 1 The Upper Gastrointestinal Tract—Esophagus and Stomach," The Microbiota in Gastrointestinal Pathophysiology, (2017), pp. 3-13.
Qin et al., "A Human Gut Microbial Gene Catalogue Established by Metagenomic Sequencing," vol. 464, (Mar. 2010), pp. 59-67.
Sender et al., "Revised Estimates for the Number of Human and Bacteria Cells in the Body," PLOS Biology, (Aug. 19, 2016), pp. 1-14.
Tripathia et al., "Identification of Human Zonulin, a Physiological Modulator of Tight Junctions, as Prehaptoglobin-2," PNAS, vol. 106, No. 39, pp. 16799-16804.
Vergauwen et al., "Confounding Factors of Ultrafiltration and Protein Analysis in Extracellular Vesicle Research," Scientific Reports, vol. 7: 2704, (2017), 12 pages.
Wispelwey et al., "Haemophilus Influenzae Outer Membrane Vesicle-Induced Blood-Brain Barrier Permeability during Experimental Meningitis," Infection Immunity, vol. 57, No. 8, (Aug. 1989), pp. 2559-2562.
Wufrel et al., "The Michigan State University Libraries are Pleased to Supply this Material to You from our Collection, The MSU Library does not Hold Copyright of This Material and Cannot Authorize any Further Reproduction," Bacterial Endotoxins: Lipopolysaccharides from Genes to Therepy, (1995), pp. 287-295.
Yanez-Mo et al., "Biological Properties of Extracellular Vesicles and Their Physiological Functions," Journal of Extracellular Vesicles, vol. 4, 27066, (2015), 62 pages.
Zitvogel et al., "Microbiome and Anticancer Immunosurveillance," Cell, vol. 165, (Apr. 7, 2016), pp. 276-287.

* cited by examiner

USE OF BACTERIAL EXTRACELLULAR VESICLES AS A BIOMARKER FOR INTESTINAL BARRIER PERMEABILITY AND MICROBIAL DYSBIOSIS

CROSS-REFERENCE TO RELATED APPLICATIONS

This application is a national phase entry under 35 U.S.C. § 371 of International Patent Application PCT/EP2019/082054, filed Nov. 21, 2019, designating the United States of America and published as International Patent Publication WO 2020/104577 A1 on May 28, 2020, which claims the benefit under Article 8 of the Patent Cooperation Treaty to European Union Patent Application Serial No. 18207847.7, filed Nov. 22, 2018.

TECHNICAL FIELD

The application relates to the field of the usage of biomarkers for disease diagnostics and monitoring. More specifically, the application relates to a method of analyzing a biofluid of a subject for the presence of bacterial extracellular vesicles (EV), the method comprising the steps of a) extracting bacterial EV from the biofluid, b) analyzing the bacterial EV-extracted molecular patterns for the presence of a disease marker, wherein the disease marker is a disease-specific molecular pattern of the subject and wherein the subject comprises patients diagnosed with inflammatory disease such as a Human Immunodeficiency Virus (HIV) infection, Inflammatory Bowel Disease (IBD) or cancer.

BACKGROUND

A number of disclosures report on the impact of gut microbiota on several aspects of health and disease due to altered intestinal permeability resulting in systemic immune activation by pathogen-associated molecular patterns (PAMP), a process termed microbial translocation.[1-4]

Common to these studies is the analysis of systemic endotoxins, lipopolysaccharide (LPS), as the major outer membrane PAMP of gram-negative bacteria, to quantitatively assess the degree of microbial translocation. While systemic LPS is typically regarded as a soluble product, either or not neutralized by lipoproteins and endotoxin core antibodies, LPS is also released as a membrane-associated PAMP through extracellular vesicles (EV).[5-7]

Bacterial EV are spherical, nanometer-sized membrane particles transporting cell signaling products, including nucleic acids, metabolites, proteins and endotoxins.[8] As such, bacterial EV that enter the systemic circulation may deliver and elicit a variety of immunological and metabolic responses in different organs including the brain.[9]

However, it is completely unknown whether the systemic presence and activity of bacterial EV in a subject can be used as a biomarker for intestinal barrier permeability and microbial dysbiosis.

DETAILED DESCRIPTION

Figure 1:
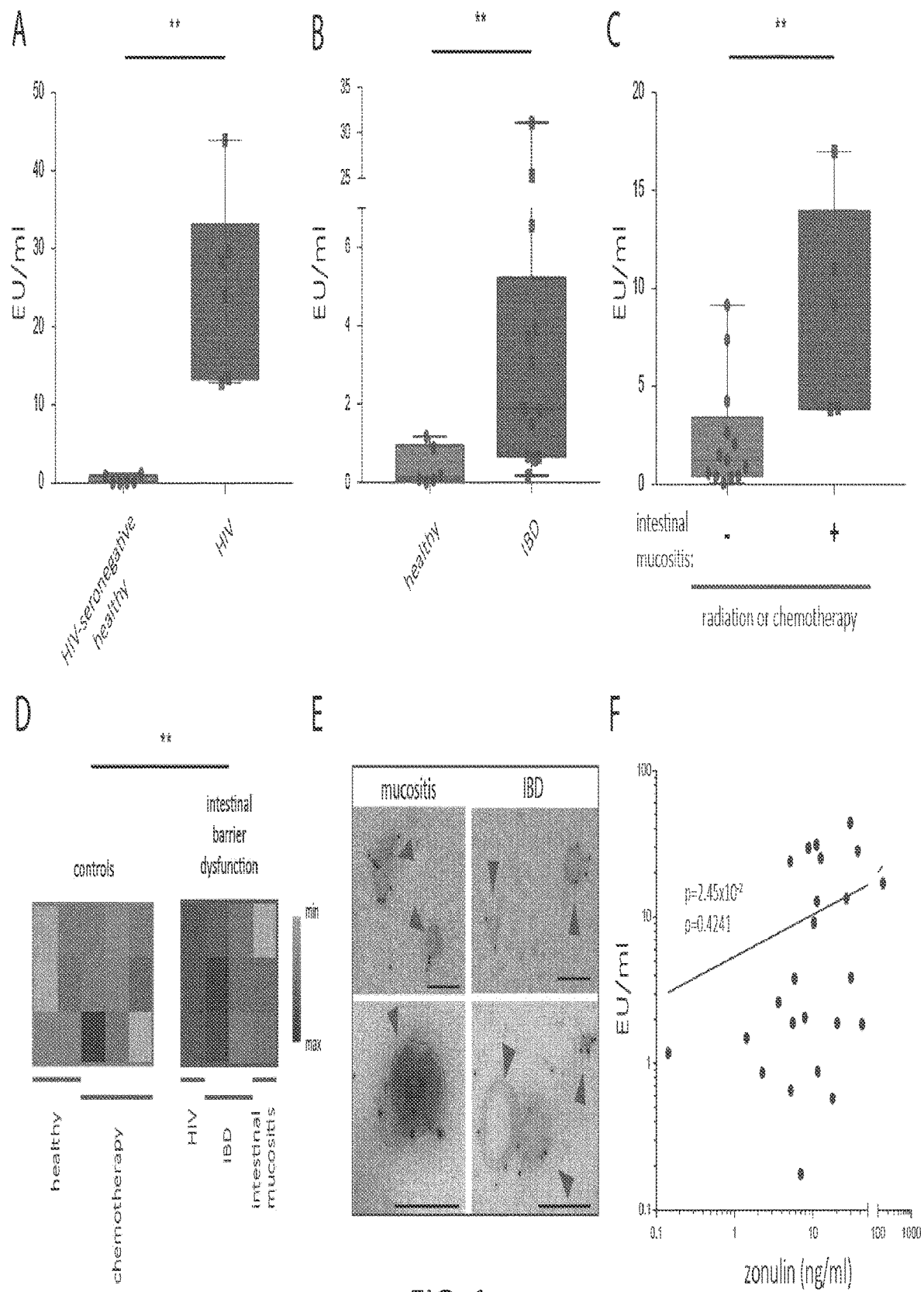
FIG. 1: Quantitative and qualitative assessment of LPS-positive bacterial EV in plasma of healthy volunteers and patients with intestinal barrier permeability. (A-C) LPS activity levels of bacterial EV isolated from plasma of patients diagnosed with HIV, IBD and therapy-induced mucositis compared to respective controls. Box and whisker plot comparison of LPS activity levels between: HIV-sero-negative controls and treatment naive HIV patients with high levels of viral replication (>$10^3$ HIV-1 RNA copies/ml); healthy volunteers and inflammatory bowel disease (IBD) patients during remission or with active disease; chemotherapy patients without gastrointestinal side effects and radiation- or chemotherapy-induced intestinal mucositis patients. The body of the box plots represents the first and third quartiles of the distribution, and the median line. The whiskers comprise the minimum and maximum values. (Mann-Whitney U test, *$p<0.05$, **$p<0.01$) (D) TLR4 agonistic activity of bacterial EV isolated from plasma of controls and patients with intestinal barrier permeability. TLR4 agonists stimulate the HEK-BLUE™-hTLR4 reporter cell line, which induces a color change of the detection medium (data were transformed into Z-scores). (E) Immune electron microscopy images of bacterial EV isolated from plasma of patients with intestinal barrier permeability (scale bar=200 nm). (F) Correlation analysis between plasma zonulin levels and bacterial EV-associated LPS levels (Spearman's $p=0.4241$, $p=2.45\times10^{-2}$).

Disclosed is that circulating bacterial EV are present in a biofluid, are able to induce immune activation and correlate with impaired barrier integrity in patients diagnosed with—but not limited to—IBD, HIV, cancer patients under chemotherapy/pelvic radiotherapy, and cancer patients with chemo/radio therapy-induced intestinal mucositis. This finding together with the documented gut dysbiosis in the patients further discloses that circulating bacterial EV are useful to determine gut microbial dysbiosis.

Therefore the disclosure relates to an in vitro method to determine intestinal barrier permeability and gut microbial dysbiosis in a subject comprising:
  providing a biofluid sample from the subject,
  isolating bacterial EV from the biofluid sample, and
  determining the level of LPS (lipopolysaccharide) and LTA (lipoteichoic acid) activity of the bacterial EV, and
  determining the 16S rRNA content of the bacterial EV, and
  determining the protein content of the bacterial EV, and
  quantifying bacterial EV number,
wherein the level of LPS and LTA activity and bacterial EV number correlate positively with intestinal barrier permeability and wherein the 16S rRNA and protein content correlate with gut microbial dysbiosis in the subject.

The term 'intestinal barrier permeability' means the ineffective monitoring of the gut mucosal surface and inability to seal the host interior against potentially harmful compounds such as bacteria, toxins and antigens present in the gastrointestinal tract.

The term 'microbial dysbiosis' means any perturbation of the normal microbiome content that could disrupt the symbiotic relationship between the host and associated microbes, a disruption that can result in diseases, such as inflammatory bowel disease and other gastrointestinal (GI) disorders, including—but not limited to—gastritis, peptic ulcer disease, irritable bowel syndrome, and even gastric and colon cancer[17]; but can also influence treatment-induced responses (for example, chemotherapy, immune therapy) in diseases such as—but not limited to—cancer, inflammatory disorders).[18-19]

The term 'subject' can be any person or patient but specifically relates to patients diagnosed—but not limited to—IBD, HIV and chemotherapy or pelvic radiation treated cancer patients with or without intestinal mucositis. Additionally, and as circulating bacterial EV can be used in the detection of gut microbial dysbiosis, the term 'subject' also specifically refers to patients having specific diseases related to gut microbiome dysbioses such as IBD, cancer, autism, obesity, diabetes, . . . .

Therefore, the disclosure relates to an in vitro method as described above wherein the subject is diagnosed with inflammatory disease including but not limited to inflammatory bowel disease, HIV and cancer wherein the subject receives or not pelvic radiation therapy, systemic chemotherapy or immunotherapy.

The term 'a biofluid sample' specifically relates to well-known biofluids such as blood, saliva, urine, cerebrospinal fluid, stool, ascites fluid, sputum, semen, breast milk or sweat.

Therefore, the disclosure specifically relates to an in vitro method as described above, wherein the biofluid sample is blood, saliva, urine, cerebrospinal fluid, stool, ascites fluid, sputum, semen, breast milk or sweat.

With regard to plasma as a biofluid, blood can be collected using different blood collection tubes (for example, citrate, EDTA, heparin). Plasma can be prepared by including one or two centrifugation steps (to remove blood cells and platelets). For example, blood is collected using citrate tubes and centrifuged 15 min at 2500 g and room temperature, resulting in platelet poor plasma (PPP). To obtain platelet free plasma (PFP), PPP can be centrifuged 15 min at 2500 g and room temperature.

Other biofluids, saliva, urine, cerebrospinal fluid, stool, sputum, semen, breast milk or sweat, can be processed in an identical manner as the processing of plasma.

To separate bacterial EV from eukaryotic EV, a density based separation technique is necessary (for example, a sucrose cushion/gradient or an iodixanol gradient). To separate bacterial EV from soluble LPS, a size based separation technique is necessary (for example, asymmetrical flow field-flow fractionation (AF4), size exclusion chromatography). For example, a combination of size exclusion chromatography and OPTIPREP™ density gradient centrifugation can be used. Alternatively, bacterial EV present in plasma can be isolated by applying an immuno-affinity based isolation protocol using a bacterial EV specific protein.

Therefore, the disclosure specifically relates to an in vitro method as described above, wherein the isolating step is undertaken by combining size- and density based separation such as size exclusion chromatography and density gradient centrifugation.

LPS activity/content can be measured by using biological activity assays, such as limulus amebocyte lysate (LAL) and LAL-like activity assays, fluorescence assays (such as ENDOLISA®, PYROGENE™, or ENDOZYME®), enzymatic tests (such as HEK-BLUE™ LPS detection kit/HEK-BLUE™ hTLR4 cells, ELISA), and mass assays [such as 3-hydroxymyristate (3HM) quantitation by GC/MS, HPLC/MS/MS]. For example, the LAL assay and HEK-BLUE™ hTLR4 cells can used.[16] (see Examples, 'material and methods': LPS measurement, quantification of TLR4 agonist activity)

LTA activity/content can be measured by using enzymatic tests (HEK-BLUE™ hTLR2 cells, ELISA) and mass assays. LTA is a major constituent of the cell wall of gram-positive bacteria and LTA activity/content measurement provides a way to perform a quantification of gram-positive EV.

Assessment of the 16S rRNA genes content by qPCR and 16S rRNA sequencing (metagenomics) can be performed for global microbiota phylogenetic profiling of bacterial EV. Small/total RNA sequencing can be performed to investigate the small/total RNA landscape of bacterial EV.

Protein content of bacterial EV can be determined by mass spectrometry analysis (such as LC-MS/MS) (metaproteomics) for global microbiota phylogenetic profiling of bacterial EV and to investigate the protein landscape of bacterial EV as is described in detail further (see Examples, 'material and methods': LC-MS/MS analysis)

Quantification of bacterial EV can be performed by high-resolution flow cytometry- and microscopy-based methods as well as particle detection by nanoparticle tracking or tunable resistive pulse sensing (TRPS) analysis (see Examples, 'material and methods': nanoparticle tracking analysis).

Therefore the disclosure further relates to an in vitro method as described above wherein the LPS and LTA activity determining step is undertaken by a reporter assay.

Furthermore, the disclosure specifically relates to an in vitro method as described above wherein the reporter assay is the limulus amebocyte lysate assay and/or the Toll-like receptor 4 assay and/or the Toll-like receptor 2 assay or any other method known in the art.

The disclosure further relates to an in vitro method as described above wherein the 16S rRNA content determining step is undertaken by 16S rRNA gene analysis such as 16S rRNA sequencing or any other method known in the art.

The disclosure further relates to an in vitro method as described above wherein the protein content determining step is undertaken by protein analysis such as mass spectrometry analysis or any other method known in the art.

The disclosure further relates to an in vitro method as described above wherein the bacterial EV number quantifying step is undertaken by flow cytometry analysis or nanoparticle tracking analysis or any other method known in the art.

The term 'a positive correlation' refers to the degree of relationship between linearly related variables, which can be measured by calculating the Pearson correlation and defining a p value <0.05 as significant.

The disclosure also relates to an in vitro method as described above for use to monitor a therapeutic response.

With the term 'monitoring a therapeutic response' is meant the following:
although more intervention trials are urgently needed, probiotics, prebiotics and particular diet can be used to influence microbial dysbiosis and intestinal barrier permeability. The disclosure relates to an in vitro method as described above for use to determine the clinical outcome and effectiveness of these therapeutic interventions.

The disclosure further relates to an in vitro method as described above wherein the therapeutic response influences intestinal barrier function and/or microbial dysbiosis.

With the term 'influencing the intestinal barrier function and/or microbial dysbiosis' is meant a positive or negative impact on the epithelial cell layer, mucosal barrier and gut immune system leading to an improvement of the systemic clinical symptoms.

Moreover, the disclosure further relates to an in vitro method to determine intestinal barrier permeability in a subject comprising:
providing a biofluid sample from the subject,
isolating bacterial EV from the biofluid,
determining the level of LPS activity and LTA-activity of the bacterial EV, and
quantifying bacterial EV number,
wherein the level of LPS and LTA activity, and bacterial number correlate positively with intestinal barrier permeability in the subject.

The present disclosure also relates to an in vitro method to determine gut microbial dysbiosis in a subject comprising:
providing a biofluid sample from the subject,
isolating bacterial EV from the biofluid sample,
determining the 16S rRNA content of the bacterial EV, and
determining the protein content of the bacterial EV
wherein the 16S rRNA and protein content correlate with gut microbial dysbiosis in the subject.

Examples

Material and Methods:
Blood and Stool Samples

Venous blood from patients and healthy volunteers was collected using VENOSAFE®-citrate tubes (VF-054SBCS07, Terumo Europe, Leuven, Belgium). Collection of blood samples was according to Ethical Committee of Ghent University Hospital approval EC/2014/0655 and EC/2017/0882 and in accordance to relevant guidelines. Participants gave written informed consent. Within 120 min after collection, whole blood was centrifuged 15 min at 2500 g and room temperature, resulting in platelet poor plasma (PPP). To obtain platelet free plasma (PFP), PPP was centrifuged 15 min at 2500 g and room temperature. Plasma (PFP) was stored by −80° C. until further use. The total time between collection and −80° C. storage was not more than 160 min. Collection of stool samples was according to Ethical Committee of Ghent University Hospital approval EC/2006/377 and in accordance to relevant guidelines. Participants gave written informed consent.

PBMC Isolation

PBMC were isolated from venous blood of healthy volunteers using FICOLL-PAQUE® PLUS (GE Healthcare Bio-Sciences, Uppsala, Sweden) according to manufacturer's protocol.

Bacterial EV Isolation from Plasma

A combination of size exclusion chromatography (SEC) and OPTIPREP™ density gradient (DG) centrifugation was used to isolate bacterial EV from plasma. SEPHAROSE® CL-2B (GE Healthcare, Uppsala, Sweden) was washed 3 times with endotoxin-free PBS (Merck Millipore, Billerica, Massachusetts, USA) containing 0.32% trisodium citrate dihydrate (CHEMCRUZ™, Dallas, Texas, USA). For preparation of the SEC column, nylon filter with 20 µm pore size (NY2002500, Merck Millipore, Billerica, Massachusetts, USA) was placed on bottom of a 10 ml syringe (BD Biosciences, San Jose, California, USA), followed by stacking of 10 ml SEPHAROSE® CL-2B. On top of the SEC column, 2 ml plasma was loaded and fractions of 1 ml eluate were collected. SEC fractions 4, 5 and 6 were pooled and concentrated to 1 ml using 10 kDa centrifugal filter (AMICON® Ultra-2 mL, Merck Millipore, Billerica, Massachusetts, USA).[12] The resulting 1 ml sample was loaded on top of a DG. This discontinuous iodixanol gradient was prepared by layering 4 ml of 40%, 4 ml of 20%, 4 ml of 10% and 3.5 ml of 5% iodixanol in a 16.8 ml open top polyallomer tube (Beckman Coulter).[11] The DG was centrifuged 18 h at 100,000 g and 4° C. using SW 32.1 Ti rotor (Beckman Coulter). Fractions of 1 ml were collected and pooled (1-5, 6-7, 8-9, 10-11, 12-13, 14-16) to obtain DG fractions 1-6. An additional SEC was performed on the pooled DG fractions to remove iodixanol.[12] SEC fractions 4-7 were pooled and concentrated to 100 µl and stored at −80° C. until further use.

Bacterial EV Isolation from Cell Culture

*Escherichia coli* Nissle 1917 (EcN) (Ardeypharm, Herdecke, Germany) were grown overnight at 37° C. in 250 ml Luria-Bertani broth (LB) with constant rotation (150 rpm). Growth was monitored by measuring the optical density at 600 nm. Bacterial cells were pelleted by centrifugation at 8000 g for 15 min at 4° C. and the obtained supernatant was filtered through a 0.22 µm pore size filter (WHATMAN®, Dassel, Germany) to remove residual bacteria. 10 kDa CENTRICON® Plus-70 centrifugal units (Merck Millipore, Billerica, Massachusetts, USA) were used to concentrate the filtered supernatant at 4° C. to 667 µl. A discontinuous iodixanol gradient was prepared by layering 4 ml of 50%, 4 ml of 40%, 4 ml of 20%, 3.5 ml of 10% iodixanol and 1 ml of PBS in a 16.8 ml open top polyallomer tube (Beckman Coulter). The 50% layer was obtained by mixing 667 µl of the sample with 3.33 ml OPTIPREP™. The DG was centrifuged 18 h at 100,000 g and 4° C. using SW 32.1 Ti rotor (Beckman Coulter). DG fractions of 1 ml were collected and DG fractions 8-9 pooled and diluted to 15 ml with PBS, followed by 3 h ultracentrifugation at 100,000 g and 4° C. using SW 32.1 Ti rotor (Beckman Coulter, Fullerton, California, USA). Resulting pellet was resuspended in 100 µl PBS and stored at −80° C. until further use.

Bacterial EV Isolation from Human Feces 50 g feces were dissolved in 250 ml PBS and centrifuged twice at 8000 g and 4° C. for 15 min. The obtained supernatant was filtered through a 0.22 µm pore size filter (Whatman, Dassel, Germany). 10 kDa CENTRICON® Plus-70 centrifugal units (Merck Millipore, Billerica, Massachusetts, USA) were used to concentrate the filtered supernatant at 4° C. to 667 µl. Similar to bacterial EV isolation from cell culture, a discontinuous iodixanol gradient was prepared by layering 4 ml of 50%, 4 ml of 40%, 4 ml of 20%, 3.5 ml of 10% iodixanol and 1 ml of PBS in a 16.8 ml open top polyallomer tube (Beckman Coulter). The 50% layer was obtained by mixing 667 µl of the sample with 3.33 ml OPTIPREP™. The DG was centrifuged 18 h at 100,000 g and 4° C. using SW 32.1 Ti rotor (Beckman Coulter, Fullerton, California, USA). DG fractions of 1 ml were collected, DG fractions 8-9 pooled and SEC was performed (similar to bacterial EV isolation from plasma). SEC fractions 4-7 were pooled and concentrated to 100 µl and stored at −80° C. until further use.

Transwell System

Caco-2 cells were grown in DMEM medium supplemented with 10% FCS, 0.01% nonessential amino acids (100×), 1% (w/v) L-Glutamine 200 mM, 100 IU/ml Penicillin and 100 µg/ml Streptomycin and were cultivated on a permeable filter support (diameter 12 mm, membrane pore size 0.4 µm, Merck KGaA, Darmstadt, Germany) for 21 days to form a monolayer, as described before.[14] Cell monolayers in transwell systems were incubated for 24 h with different concentrations of dextran sulfate sodium salt (DSS, MW=40000, Merck KGaA, Darmstadt, Germany) in DMEM to the apical side. After removing the apical medium, $1.5 \times 10^{11}$ stool bacterial EV were placed to the apical side and basolateral bacterial EV were isolated after 24 h (see 'bacterial EV isolation from cell culture').

Western Blotting

All fractions and pellets were dissolved in reducing sample buffer (0.5M Tris-HCl (pH 6.8), 40% glycerol, 9.2% SDS, 3% 2-mercaptoethanol, 0.005% bromophenol blue) and boiled at 95° C. during 5 min. Proteins were separated by SDS-polyacrylamide gel electrophoresis and transferred to nitrocellulose membranes (Bio-Rad, Hercules, California, USA). After blocking the membranes, blots were incubated overnight with primary antibodies. Antibodies against *E. coli* LPS (1:1000, Abcam, Cambridge, UK), OmpA (1:5000, Antibody Research Corporation, Missouri, USA), Alix (1:1000, 3A9, Cell Signaling Technology, Beverly, Massachusetts, USA), Flotillin-1 (1:1000, 610820, BD Biosciences, Franklin Lakes, New Jersey, USA) and CD9 (1:1000, D3H4P, Cell Signaling Technology, Beverly, Massachusetts, USA) were used. Incubation with secondary antibodies was performed after extensive washing of the membranes in PBS with 0.5% Tween20. After final extensive washing, chemiluminescence substrate (WESTERNBRIGHT® SIRIUS®, Advansta, Menlo Park, California, USA) was added and imaging was performed using Proxima 2850 Imager (IsoGen Life Sciences, De Meern, The Netherlands).

Coomassie Brilliant Blue Staining

The bacterial EV pellet was dissolved in reducing sample buffer (1M Tris-HCl (pH 6.8), 30% glycerol, 6% SDS, 3% 2-mercaptoethanol, 0.005% bromophenol blue) and boiled at 95° C. during 5 min. Proteins were separated by SDS-polyacrylamide gel electrophoresis. Gel was stained with Coomassie Brilliant Blue R-250 (Bio-Rad, Hercules, California, USA) during 1 h followed by destaining overnight at 4° C. with Coomassie Brilliant Blue destaining solution (Bio-Rad).

Nanoparticle Tracking Analysis

Aliquots of isolated particles were used for Nanoparticle Tracking Analysis (NTA) using NanoSight LM10 microscope (NanoSight Ltd, Amesbury, UK) equipped with 405 nm laser. For each sample, three videos of 60 s were recorded and analyzed with camera level 13 and detection threshold 3. Temperature was monitored during recording. Recorded videos were analyzed with NTA Software version 3.0. For optimal measurements, samples were diluted with PBS until particle concentration was within the concentration range of NTA Software ($3\times10^8$-$10^9$ particles/ml).

Confocal Fluorescence Microscopy

Caco-2 cell monolayers were fixed in 3% paraformaldehyde for 20 min at room temperature. Following permeabilization with 0.2% (w/v) TRITON™ X-100 for 5 min, sections were blocked with 5% BSA and tight junctions labeling was performed with primary anti-ZO-1 mouse monoclonal antibodies (Invitrogen, Rockford, USA) 2.5 µg/ml and secondary ALEXA FLUOR™ 488 goat anti-rabbit IgG antibodies (Invitrogen, Rockford, USA) 1 µg/ml for 1 h at room temperature. Nuclei were stained with 0.4 µg/ml DAPI. The fluorescence was examined by using a Leica DMI60000 confocal microscope (40× objective lens) coupled to an Andor DSD2 scanner and a Zyla 5.5 CMOS camera.

Electron Microscopy

Samples were deposited on FORMVAR® carbon coated, glow-discharged grids. After 20 min, the grids were incubated in a blocking serum containing 1% BSA in PBS. Antibodies and gold conjugates were diluted in 1% BSA in PBS. In case of immunostaining, the grids were exposed to the primary mouse anti-*E. coli* LPS antibody (10 mg/ml) for 20 min, followed by rabbit anti-mouse secondary antibody (Zymed) for 20 min and protein A-gold complex (10 nm size) (Center for Molecular Medicine, Utrecht, the Netherlands) for 20 min. The blocking efficiency was controlled by performing the labelling procedure in the absence of primary antibody. The grids were stained with neutral uranylacetate and embedded in methylcellulose/uranyl acetate and examined in a TECNAI™ Spirit transmission electron microscope (Thermo Fisher Scientific FEI). Images were captured by Quemesa charge-coupled device camera (Olympus Soft Imaging Solutions).

LC-MS/MS Analysis

Samples were processed for LC-MS/MS by filter-aided sample preparation (FASP). Lysates were prepared by mixing samples with SDT-lysis buffer (2% SDS, 500 mM Tris-HCL (pH 7.6), 0.5 M DTT) at a 4:1 sample to buffer ratio and incubated at 95° C. for 5 min. After clarification of lysates by centrifugation (16,000 g for 5 min), samples were mixed with 300 µli UA (8 M urea, 0.1 M Tris-HCl (pH 8.5)) in a MICROCON™ YM-10 centrifugal filter device (Merck KGaA, Darmstadt, Germany). Filters were centrifuged twice (14,000 g for 40 min at 20° C.) with the addition of 200 µl UA in between. Proteins were alkylated by addition of 100 µl IAA solution (0.05 M iodoacetamide in UA buffer) and incubated for 30 min at room temperature, followed by centrifugation. This was followed twice by addition of 100 µl UA and twice by addition of 100 µl DB buffer (1 M urea, 0.1 M Tris-HCl (pH 8.5), with centrifugation in between. Filter units were transferred to new collection tubes and proteins were resuspended in 40 µL DB with Trypsin/Lys-C mix (Promega, Madison, Wisconsin, USA) for overnight proteolytic digestion at 37° C. Digests were collected by addition of 100 µl DB and centrifugation for 15 min at 14,000 g. This step was repeated once. Collected peptides were acidified with 1% trifluoroacetic acid to a pH of 2-3, followed by desalting with C18-StageTips (C18 EMPORE™ Disks, 3M, St. Paul, Minnesota, USA).

Desalted peptides were vacuum dried, dissolved in 0.1% formic acid and analyzed by LC-MS/MS. Equal amounts of peptides of each sample (300 ng) were loaded on a nanoflow HPLC system (EASY-NLC™ 1000, Thermo Fisher Scientific, Waltham, Massachusetts, USA) coupled to a Q EXACTIVE™ HF HYBRID QUADRUPOLE-ORBITRAP™ Mass Spectrometer (Thermo Fisher Scientific, Waltham, Massachusetts, USA) equipped with a nano-electrospray ionization source. The mobile phase consisted of 0.1% formic acid (solvent A) and acetonitrile/water (95:5 (v/v)) with 0.1% formic acid (solvent B). The peptides were separated with a 50 min gradient from 8 to 35% of solvent B. Before the end of the run, the percentage of solvent B was raised to 100% in 5 min and kept there for 5 min. Full MS scan over the mass-to-charge (m/z) range of 300-1750 with a resolution of 120,000, followed by data dependent acquisition with an isolation window of 2.0 m/z and a dynamic exclusion time of 30 s was performed. The top 12 ions were fragmented by higher energy collisional dissociation (HCD) with a normalized collision energy of 27% and scanned over the m/z range of 200-2000 with a resolution of 15,000. After the MS2 scan for each of the top 12 ions had been obtained, a new full mass spectrum scan was acquired and the process repeated until the end of the 60-min run. Three repeated runs per sample were performed.

Tandem mass spectra were searched using the MaxQuant software (version 1.5.2.8) against a database containing both reviewed (SwissProt) and unreviewed (TrEMBL) sequences of *Homo sapiens* and common gut microbes (Prevotella, Bacteroides, Clostridiales and Mitsuokella; based on the frequent microbe proteins dataset provided by Qin et al.), including different isoforms, of UniProtKB release 2018_07.[15] Peptide-spectrum-match- and protein-level false discovery rates were set at 0.01. Carbamidomethyl (C), as a fixed modification, and oxidation (M) and acetylation of the protein N-terminus as dynamic modifications were included. A maximum of two missed cleavages was allowed. The LC-MS profiles were aligned, and the identifications were transferred to non-sequenced or non-identified MS features in other LC-MS runs (matching between runs). The protein was determined as detected in the sample if its identification had been derived from at least two unique peptide identifications. Filtering for contaminating proteins, reverse identification and identification by site was used.

LPS, ApoA1, ApoB, ZO-1 and Cytokine/Chemokine Measurements

Quantification of ApoA1, ApoB and ZO-1 was performed using HUMAN APOLIPOPROTEIN A-I QUANTIKINE™ ELISA Kit (R&D Systems, Minneapolis, USA), Apolipoprotein B (APOB) Human SIMPLESTEP ELISA® Kit (Abcam, Cambridge, UK) and Human Zonulin ELISA Kit (Biomatik, Cambridge, Canada), respectively, according to manufacturer's protocol. LPS activity levels were measured using the Limulus Amebocyte Lysate (LAL) assay (Associates of Cape Cod, Massachusetts, USA) according to manufacturer's protocol. The human cytokine/chemokine luminex array 65-plex panel (Eve Technologies, Calgary, Canada) was used to determine the chemokine/cytokine concentration in the samples.

Quantification of TLR4/TLR2 Agonist Activity

HEK-BLUE™-hTLR4 and HEK-BLUE™-hTLR2 reporter cell lines were obtained from InvivoGen (Toulouse, France). Isolated bacterial EV were added to the reporter cell line and incubated with HEK-BLUE™ detection medium according to manufacturer's protocol.

Statistical Data Analysis/Illustrations

The experimental data were analyzed with GraphPad Prism 7. Mann-Whitney U tests were performed to compare non-normally distributed continuous variables. Pearson r correlation was calculated to measure the degree of relationship between linearly related variables. Spearman rank correlation was calculated to measure the degree of association between two variables. ANOVA was used for comparison between multiple groups. A p value <0.05 was defined as significant (*$p<0.05$, $p<0.01$, *$p<0.001$). Illustrations were made in Adobe Illustrator CS6.

DNA Isolation and qPCR

DNA is isolated using the QIAAMP® POWERFECAL® DNA kit with an additional incubation step of 10 minutes at 95° C. Each sample is added to a well of a 384 multiwell plate. Per well, 3 µL of mastermix is used that contains 2.5 µL of SSOADVANCED™ UNIVERSAL SYBR® Green Supermix, 0.25 µL of forward primer (5 µM) and 0.25 µL of reverse primer (5 µM). 2 µL of every DNA sample is added to each well. The plate is sealed and centrifuged for 5 minutes at 300 g at room temperature. In the Roche LIGHTCYCLER® 480, the DNA is amplified.

RNA Isolation, Total RNA Library Preparation and Sequencing

RNA isolation was performed using the miRNeasy Serum/Plasma Kit (Qiagen). On the total amount of 12 µl eluate, gDNA heat-and-run removal was performed by adding 1 µl of HL-dsDNase (ArcticZymes 70800-202, 2 U/µl) and 1 µl reaction buffer (ArcticZymes 66001). Of the resulting volume, 4 µl was used as input for the total RNA library preparation protocol. Sequencing libraries were generated using SMARTER® Stranded Total RNA-Seq Kit v2—Pico Input Mammalian (Takara, 634413). Compared to the manufacturer's protocol, the fragmentation step was set to 4 min at 94° C., hereafter the option to start from highly degraded RNA was followed. Library quality control was performed with the Fragment Analyzer high sense small fragment kit (Agilent Technologies, sizing range 50 bp-1000 bp). Based on Qubit concentration measurements or KAPA qPCR, samples were pooled and loaded on the NextSeq 500 (Illumina) with a loading concentration of 1.1 or 1.2 pM. Paired end sequencing was performed (2×75 bp) with median depth of 15.3 million reads per sample.

Results

Plasma samples of 50 subjects were fractionated to distinguish bacterial EV-associated LPS from other LPS products. The following table summarizes individual patient characteristics; 26 donors asymptomatic of intestinal barrier permeability (13 healthy volunteers and 13 cancer patients during chemotherapy without gastrointestinal side effects suggestive for intestinal mucositis) and 24 patients with clinically well-defined intestinal barrier permeability (13 inflammatory bowel disease (IBD) patients, 5 cancer patients with radiation- or chemotherapy-induced intestinal mucositis and 6 treatment naive HIV patients with high viral load):

TABLE

Baseline clinical characteristics of the subjects included in this study

| Baseline clinical characteristics | CONTROL (N = 26) | | INTESTINAL BARRIER PERMEABILITY (N =24) | | |
|---|---|---|---|---|---|
| | Healthy | Chemotherapy | IBD | Mucositis | HIV |
| Male/female (%) | 4/9 (30.8/69.2) | 0/13 (0/100) | 6/7 (46.2/53.9) | 0/5 (0/100) | 6/0 (100/0) |
| Age* (min-max) | 36 (24-59) | 53 (43-72) | 35 (25-57) | 58 (49-69) | 39 (26-59) |
| Ulcerative colitis (UC)/ Crohn's disease (CD) (%) | | | 3/7 (30/70) | | |
| Disease activity at blood sampling: active/remission (%) | | | 7/6 (53.9/46.2) | | |
| Maximum disease location (Montreal classification) (CD) | | | | | |
| L1 ileal (%) | | | 0 (0) | | |
| L2 colonic (%) | | | 1 (10) | | |
| L3 ileocolonic (%) | | | 5 (50) | | |
| L4 isolated upper disease (%) | | | 1 (10) | | |

TABLE-continued

Baseline clinical characteristics of the subjects included in this study

| Baseline clinical characteristics | CONTROL (N = 26) | | INTESTINAL BARRIER PERMEABILITY (N =24) | | |
|---|---|---|---|---|---|
| | Healthy | Chemotherapy | IBD | Mucositis | HIV |
| Disease behaviour at blood sampling (UC) | | | | | |
| E1 proctitis (%) | | | 0 (0) | | |
| E2 left sided colitis (%) | | | 2 (20) | | |
| E3 pancolitis (%) | | | 1 (10) | | |
| Radiation-/chemotherapy-induced mucositis (%) | | | | 2/3 (40/60) | |
| Viral replication (log HIV-1 RNA copies/ml) | | | | | 3.04-7.00 |
| Immune status monitoring | | | | | |
| CD4, cells/μL* (min-max) | | | | | 777.5 (199-881) |
| CD8, cells/μL* (min-max) | | | | | 675.5 (263-1450) |
| NK, cells/μL* (min-max) | | | | | 275.0 (170-708) |
| CRP, mg/L* (min-max) | | 1.7 (<0.6-148.3) | | | 1.25 (0.8-2.9) |

Figure 2:
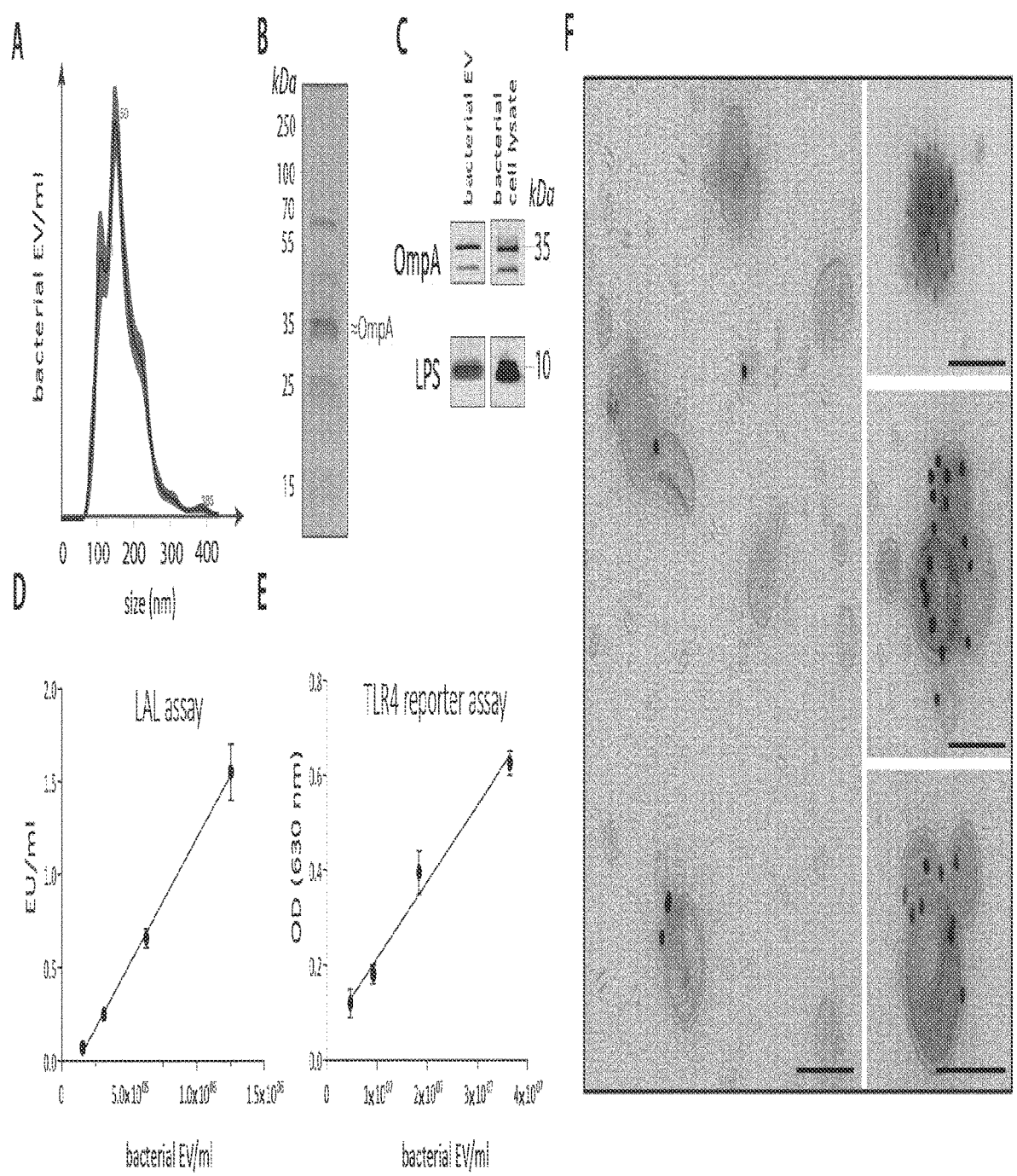
FIG. 2: Evaluation of quantitative and qualitative methods to characterize LPS-positive bacterial EV from *Escherichia coli* Nissle 1917 (EcN), a nonpathogenic gram-negative strain. (A) Size distribution of bacterial EV obtained by nanoparticle tracking analysis. (B) SDS polyacrylamide gel electrophoresis and coomassie blue staining of bacterial EV identified protein bands characteristic of outer membrane protein A (OmpA) and other porins. (C) Western blot analysis of OmpA and LPS in bacterial EV or bacterial cell lysate. (D-E) The Limulus Amebocyte Lysate (LAL) and TLR4 reporter assay quantify LPS and TLR4 agonistic activity, respectively. TLR4 agonists stimulate the HEK-BLUE™-hTLR4 reporter cell line, which induces a color change of the detection medium (optical density (OD) measurement at 630 nm). Within the detection range of the assay, a linear relationship exists between LPS (EU/ml) or TLR4 activity (OD 630 nm) and bacterial EV concentration (three technical replicates, LAL: Pearson's $r=0.9994$; TLR4 reporter: Pearson's $r=0.9814$). (F) Immune electron microscopy images of purified bacterial EV using gold-conjugated protein A to detect secondary antibodies against primary antibodies recognizing lipopolysaccharide (LPS) (scale bar=200 nm).
Figure 3:
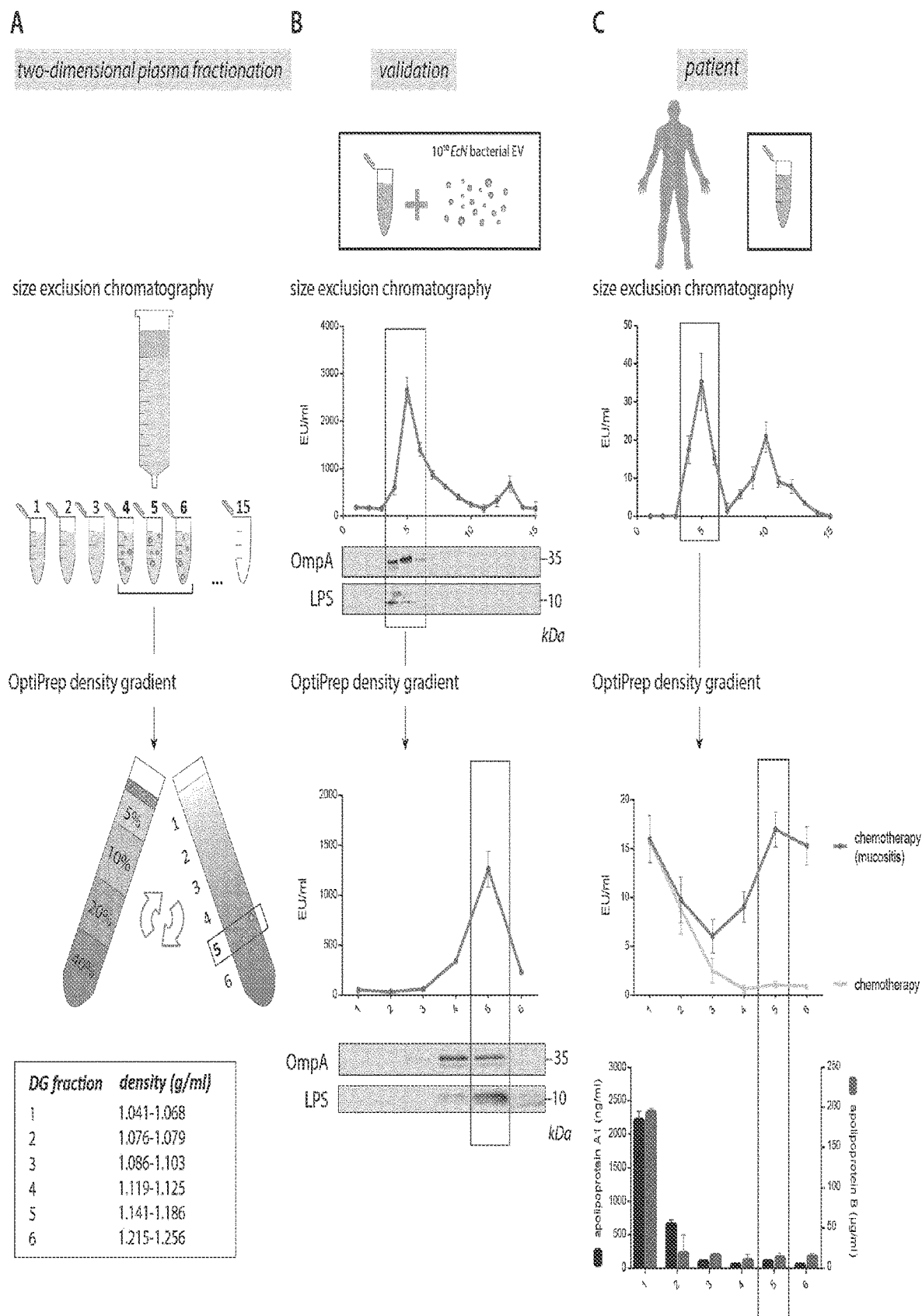
FIG. 3: Two-dimensional fractionation of plasma (size and density) separates bacterial EV-associated LPS from other LPS products. (A) A combination of size exclusion chromatography (SEC) and density gradient (DG) centrifugation is used to isolate bacterial EV from plasma. (B) 2 ml plasma, spiked with $1\times10^{10}$ EcN bacterial EV, was applied on top of the SEC column and fractions of 1 ml were collected. Bacterial EV elute in SEC fractions 4-6 as visualized by Western blot and LPS activity levels (EU/ml). SEC fractions 4-6 were concentrated to 1 ml and applied on top of a DG. During centrifugation at 100,000 g for 18 h, bacterial EV mainly float to DG fraction 5 (1.141-1.186 g/ml). (C) 2 ml plasma of a breast cancer patient with chemotherapy-induced intestinal mucositis was applied on top of the SEC column and fractions of 1 ml were collected. Bacterial EV elute in SEC fractions 4-6 as visualized by LPS activity levels (EU/ml). SEC fractions 4-6 were concentrated to 1 ml and applied on top of a DG. DG centrifugation at 100,000 g for 18 h revealed enrichment of bacterial EV-associated LPS in DG fraction 5 (1.141-1.186 g/ml) compared to respective control. An enzyme-linked immunosorbent assay (ELISA) for apolipoprotein A1 and B identified HDL and LDL in the lowest DG fractions (1.041-1.079 g/ml), indicating that these fractions contain other LPS products such as lipoprotein-associated LPS. Of note, eukaryotic EV are enriched in DG fraction 3 (1.086-1.103 g/ml).[11-12]

Bacterial EV-associated LPS and other LPS products were quantitatively measured by performing Limulus Amebocyte Lysate (LAL) and Toll-like receptor 4 (TLR4) reporter assays and qualitatively confirmed the results by immune electron microscopy (see FIG. 2). Size exclusion chromatography (SEC) and density gradient (DG) centrifugation were combined to fractionate plasma LPS in two dimensions to separate bacterial EV-associated LPS from other LPS products (see FIG. 3).

Figure 4:
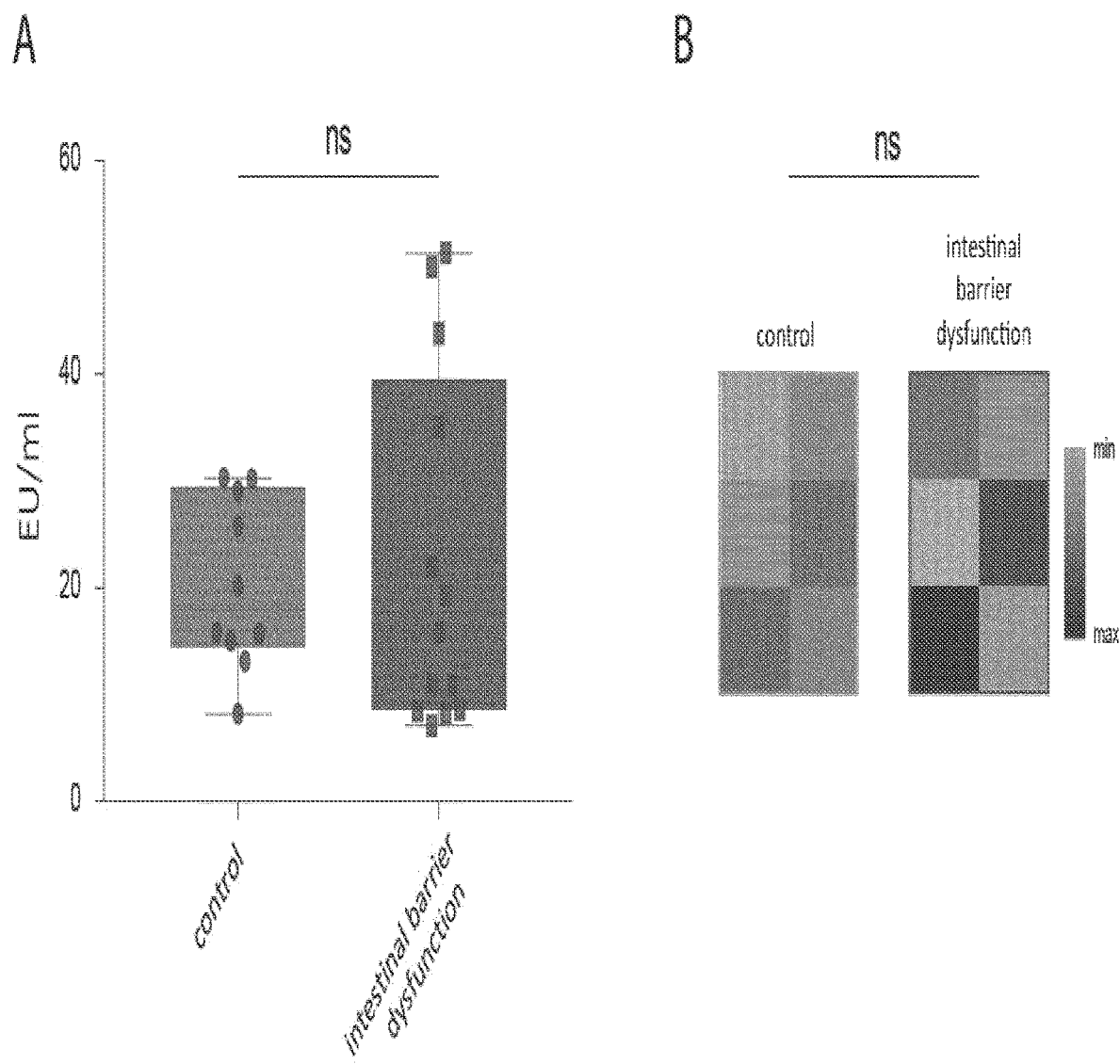
FIG. 4: Quantitative assessment of LPS products in lower density fractions (1.041-1.068 g/ml) in plasma of healthy volunteers and patients with intestinal barrier permeability. Both LAL (A) and TLR4 reporter assay (B) of the lower density fractions revealed no significant difference.

LAL analysis of DG fraction 5 (1.141-1.186 g/ml), corresponding to the density of bacterial EV (see FIG. 3), demonstrated significantly increased LPS activity in patients diagnosed with HIV, IBD and therapy-induced intestinal mucositis compared to respective controls (FIGS. 1A-1C). LAL analysis of the lower density fractions (1.041-1.068 g/ml) containing other LPS products revealed—surprisingly—no significant difference (see FIG. 4). In accordance, elevated amounts of microbial pattern recognition receptor (PRR) ligands were detected by determining the TLR4 agonistic activity in DG fraction 5 of patients with intestinal barrier permeability (FIG. 1D). Immune electron microscopy confirmed bacterial EV-associated LPS in DG fraction 5 (FIG. 1E).

Figure 5:
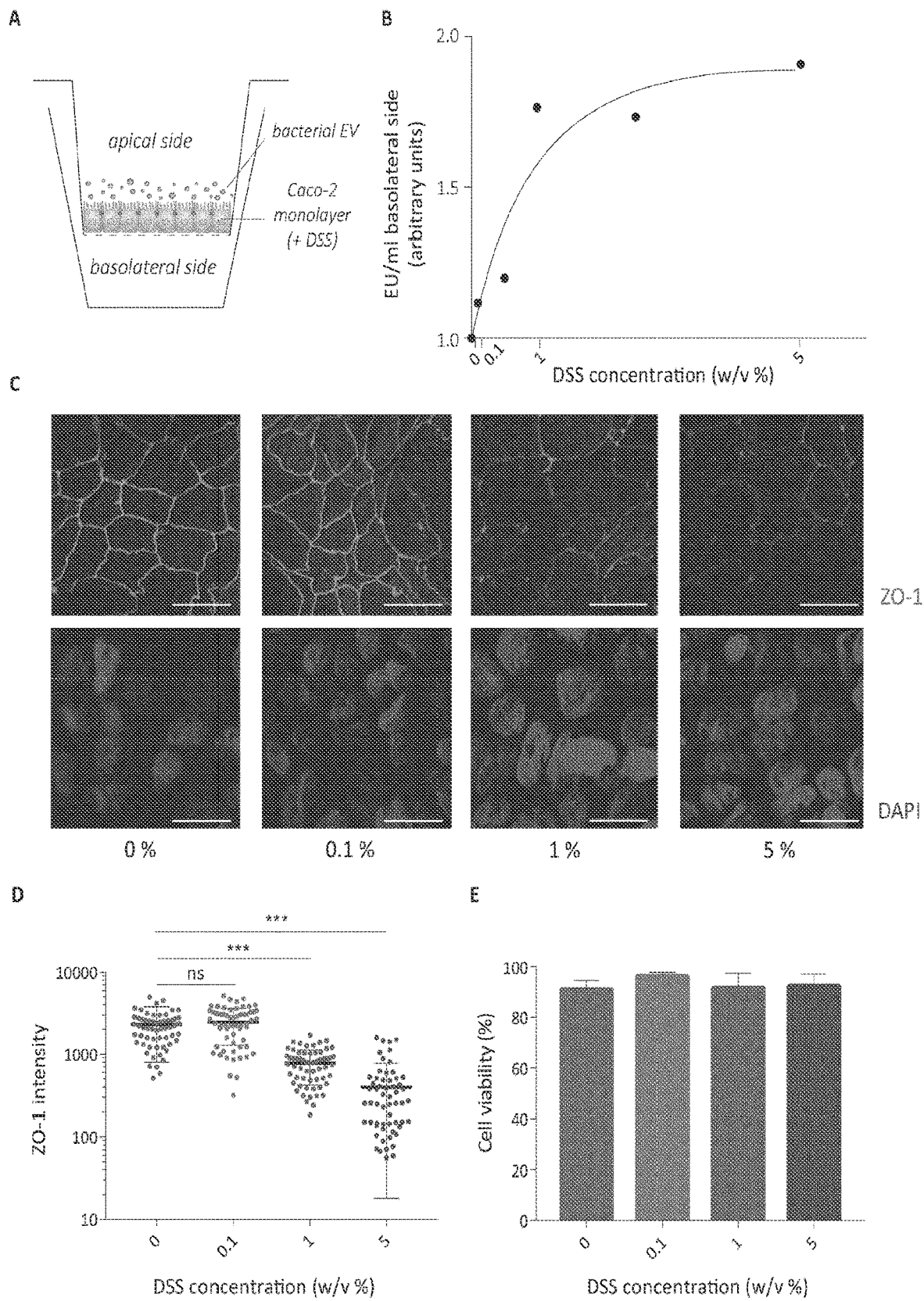
FIG. 5: Paracellular translocation of bacterial EV across a Caco-2 monolayer. (A) A Caco-2 monolayer was grown on a permeable transwell filter support and challenged with dextran sulfate sodium (DSS) to mimic colitis. $1.5 \times 10^{11}$ bacterial EV isolated from stool (see FIG. 6) were applied to the apical side and translocation was investigated by isolating and quantifying the bacterial EV present in the basolateral medium. (B) After basolateral bacterial EV isolation, LPS activity was measured as a direct marker for bacterial EV translocation using the LAL assay. (C) Caco-2 monolayers were fixed and tight junctions were labeled with ZO-1 antibodies (green) (scale bar=20 μm). (D) The tight junction integrity was assessed through high-throughput analysis of the intensity of ZO-1 staining and a clear DSS-induced tight junction disruption and barrier permeability was evidenced (ANOVA, ***$p<0.001$). (E) Cell death was not affected during challenging with DSS.
Figure 6:
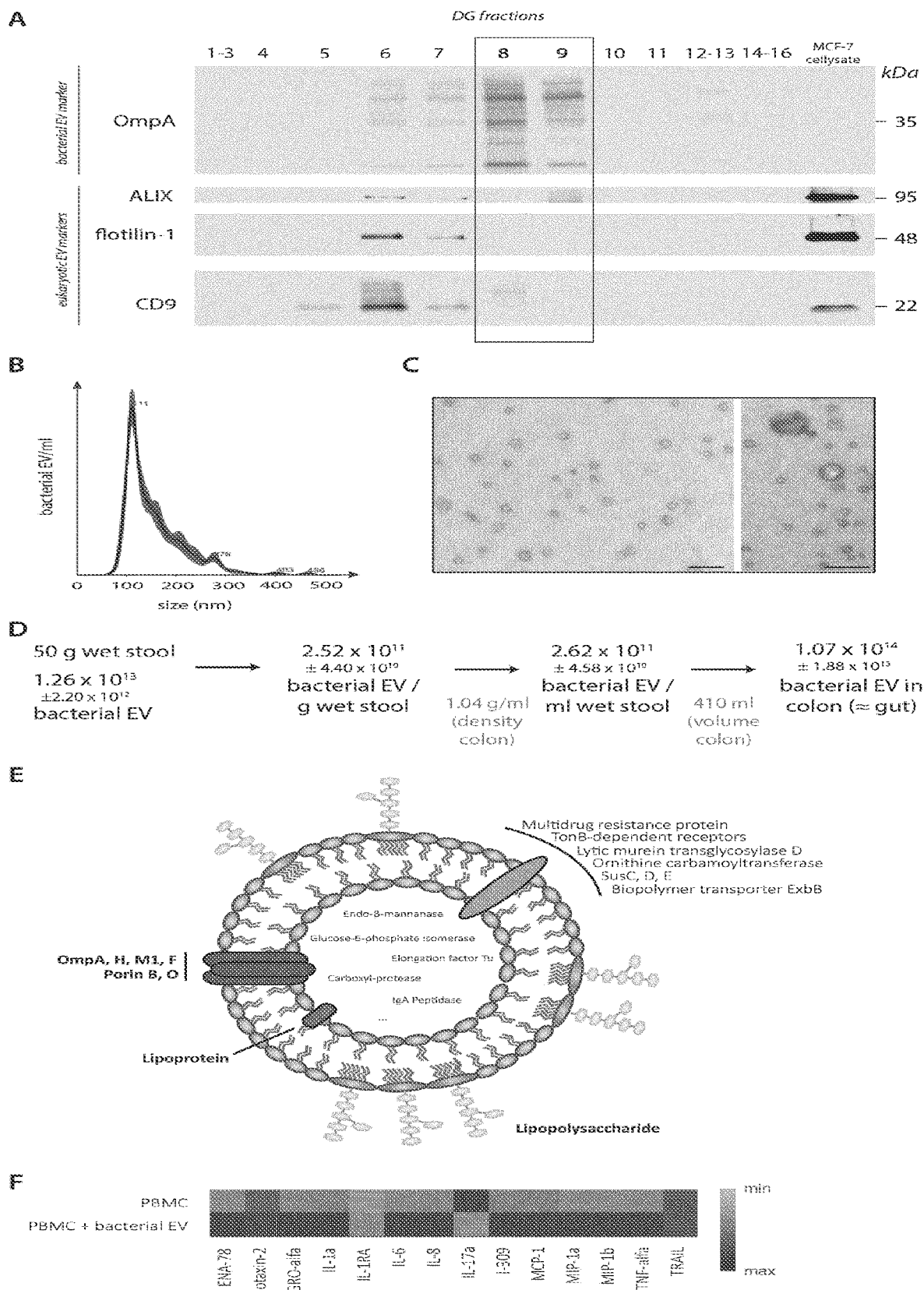
FIG. 6: Characterization of gut bacteria-derived EV isolated from healthy donor feces. (A) Western blot analysis after density gradient (DG) centrifugation revealed the presence of both eukaryotic and bacterial EV in fecal samples. Alix, Flotillin-1 and CD9 were used as eukaryotic EV markers and outer membrane protein A (OmpA) as bacterial EV marker. Note the cross-specificity of the OmpA antibody with all different forms of outer membrane proteins present in the heterogeneous bacterial EV fractions. (B) Size distribution of feces-derived bacterial EV obtained by nanoparticle tracking analysis. (C) Electron microscopy images of feces-derived bacterial EV (scale bar=200 nm). (D) Calculation of the number of bacterial EV in the human gut based on Sender et al. (three biological replicates).[13] (E) Proteomic analysis of feces-derived bacterial EV (three technical replicates). (F) Stimulation of peripheral blood mononuclear cells (PBMC) indicates the immunogenicity of bacterial EV (data obtained by luminex assay were transformed into Z-scores).

Zonulin, a biomarker of barrier integrity, initiates phosphorylation of zonula occludens proteins and leads to tight junction disassembly and increased intestinal permeability.[10] The level of bacterial EV-associated LPS significantly correlated with plasma zonulin levels, suggesting an association with intestinal barrier integrity (FIG. 1F). Indeed, compromising tight junction integrity in an in vitro colitis model using Caco-2 intestinal epithelial cells induced paracellular translocation of bacterial EV (see FIG. 5). It has been calculated that the human gut harbors at least $10^{14}$ bacterial EV, which may serve as a substantial source of systemic PAMP (see FIG. 6). Additionally, bacterial EV strongly stimulated secretion of pro-inflammatory cytokines (such as IL-6, IL-8, MCP-1 and MIP-1α) by peripheral blood mononuclear cells (PBMC) whereas the secretion of receptor antagonists (such as IL-1RA) was not stimulated, indicating potent systemic aspects (see FIG. 6F).

Figure 7:
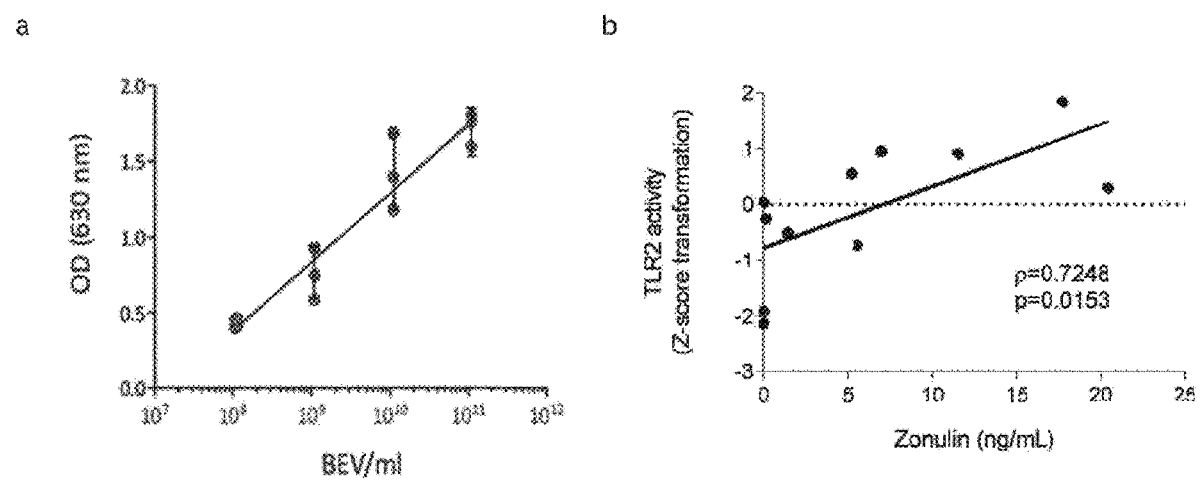
FIG. 7: (A) Within the detection range of the TLR2 reporter assay, a linear relationship exists between TLR2 activity (OD 630 nm) and bacterial EV logarithmic concentration (data points of three technical replicates and error bars (SD) are represented, Pearson's $r=0.9145$). The results are obtained by using stool-derived bacterial EV. (B) TLR2 activity of the isolated bacterial EV (after a Z-score transformation) correlates with intestinal barrier dysfunction determined by performing a Human Zonulin ELISA Kit on plasma samples (Spearman's $r=0.7248$).

Identical to the correlation analysis between the LPS activity and intestinal barrier permeability, a correlation analysis is performed between the LTA activity and intestinal barrier permeability. LTA activity is determined by performing a Toll-like receptor 2 assay on the isolated bacterial EV from biofluid. Intestinal barrier permeability is determined by performing a Human Zonulin ELISA Kit on plasma samples (see FIG. 7).

Figure 8:
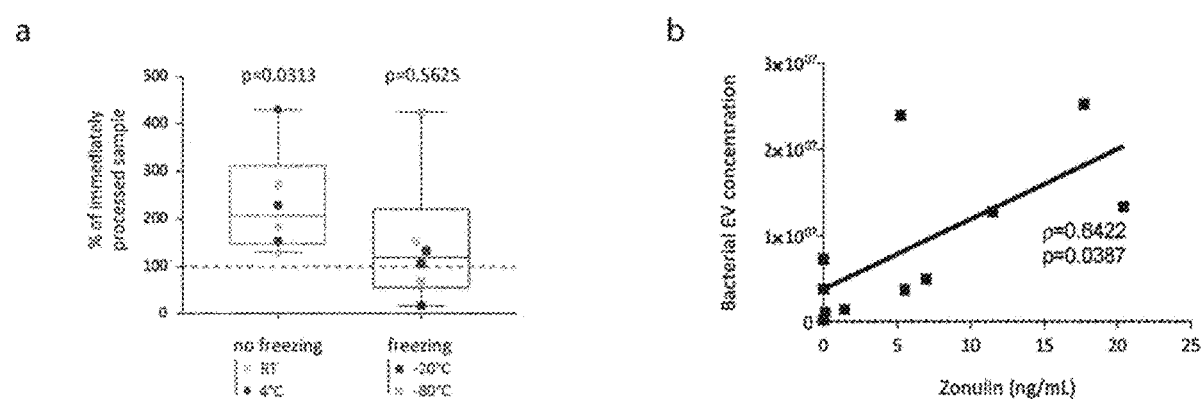
FIG. 8: (A) Bacterial EV isolation is performed on three different biological replicates of stool samples stored for 24 h at RT or 4° C. (no freezing) and −20° C. or −80° C. (freezing). The y-axis represents the percentage of final bacterial EV concentration when bacterial EV were isolated from the same stool sample but immediately after collection. The body of the box plots represents the first and third quartiles of the distribution, and the median line. The whiskers comprise the minimum and maximum values. In case of storage without freezing, the final bacterial EV concentration is significantly increased compared to immediate processing due to ex vivo bacterial EV production in non-freezing conditions (p=0.0313, One-Sample Wilcoxon Signed Rank Test). (B) Correlation analysis between bacterial EV concentration (calculated by performing a TLR4 reporter assay using a bacterial EV standard curve) and intestinal barrier dysfunction determined by performing a Human Zonulin ELISA Kit on plasma samples (Spearman's $r=0.6422$).

Identical to the correlation analysis between the LPS activity and intestinal barrier permeability, a correlation analysis is performed between the bacterial EV number and intestinal barrier permeability. Bacterial EV number can be quantified by performing Nanoparticle tracking analysis (see FIG. 6B) of the isolated bacterial EV from biofluid. Note the storage condition of the biofluid (e.g., stool) determines the final bacterial EV recovery (see FIG. 8A). Intestinal barrier permeability is determined by performing a Human Zonulin ELISA Kit on plasma samples. In FIG. 8B the bacterial EV concentration is calculated by performing a TLR4 reporter assay using a bacterial EV standard curve.

Figure 9:
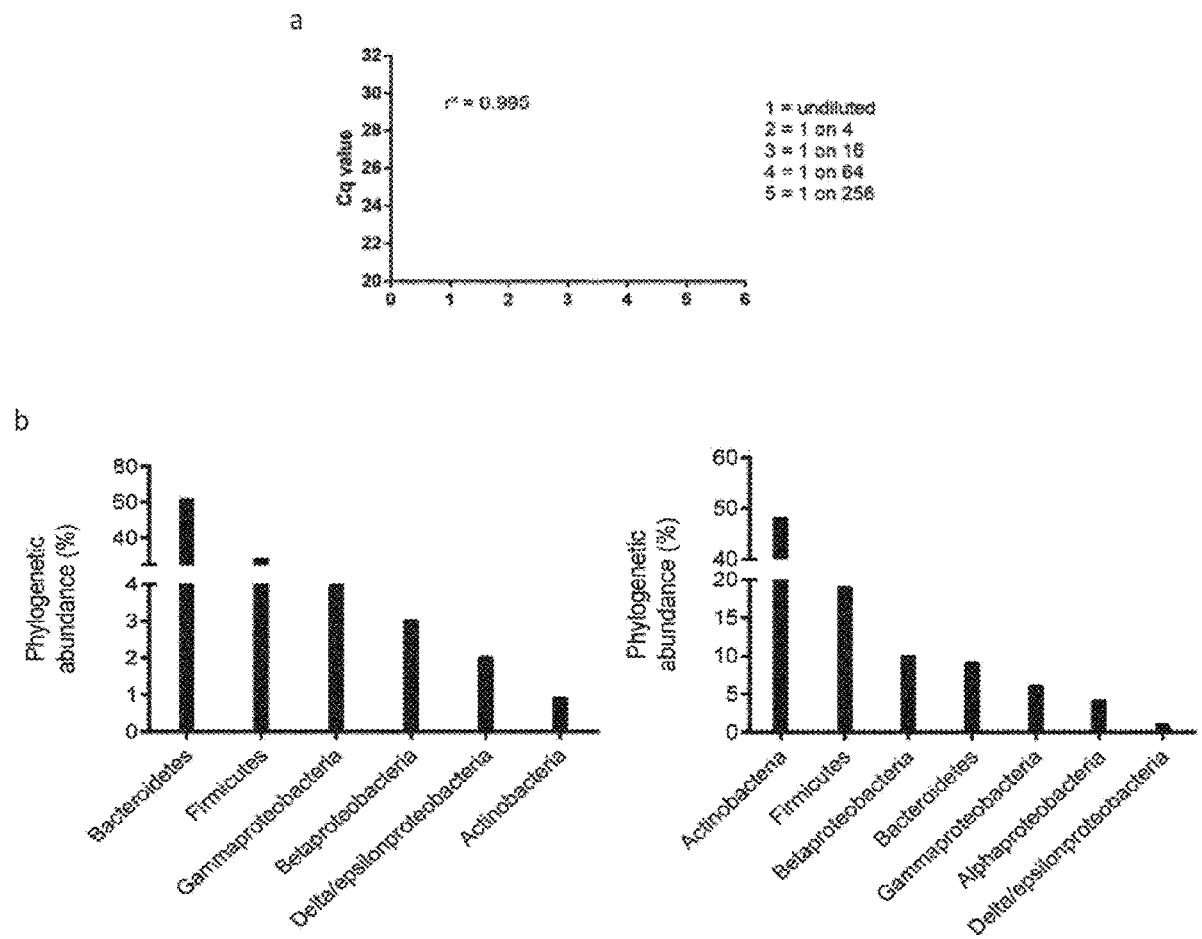
FIG. 9: (A) After DNA extraction of bacterial EV, qPCR amplification of bacterial 16S rRNA genes is performed. (B) Taxonomic identification of the bacterial RNA content in stool-derived bacterial EV (left) or blood-plasma derived bacterial EV (right) reveals a correlation between gut microbial dysbiosis (as reflected by the stool-derived bacterial EV) and blood-plasma derived bacterial EV.

The (16S r)RNA content of bacterial EV is correlated to microbial dysbiosis. Bacterial EV are isolated from the biofluid, DNA or RNA is extracted and 16S rRNA sequencing or total RNA sequencing is performed. Taxonomy of the reads is identified, revealing the bacterial EV composition. Microbial dysbiosis is evaluated by performing 16S rRNA sequencing of DNA extracted from fecal material or total RNA sequencing of RNA extracted from fecal material and correlated to the bacterial EV 16S rRNA or total RNA composition (see FIG. 9).

Figure 10:
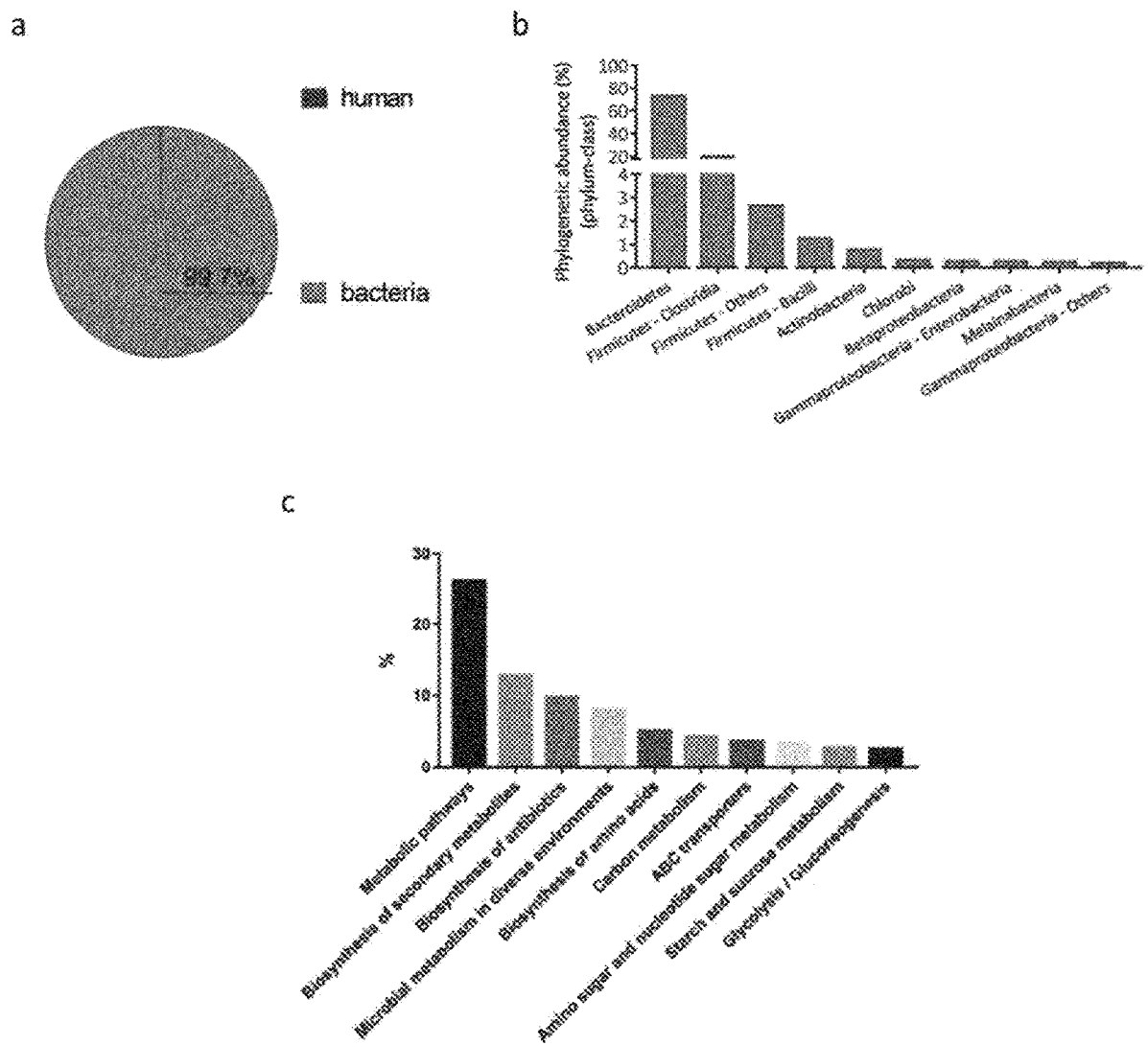
FIG. 10: (A) Metaproteomic analysis revealed a high specificity of the isolation protocol for bacterial proteins from bacterial EV and a low specificity for other human contaminants present in stool samples. 99.7% of the proteins detected in the samples with bacterial EV isolated from stool samples have a bacterial origin, and only 0.3% of the proteins a human origin. (B) Taxonomic identification of the bacterial proteins present in the samples with stool-derived bacterial EV. (C) Identification of the enriched functional pathways of bacterial proteins present in samples with blood plasma-derived bacterial EV. Gut microbial dysbiosis is reflected in the different expression of these functional pathways or in a taxonomic shift of the bacterial proteins.

The protein content of bacterial EV is correlated to microbial dysbiosis. Bacterial EV are isolated from the biofluid and LC-MS/MS analysis performed. Taxonomy of the proteins is identified, revealing the bacterial EV composition (see FIG. 10B). An identification of the enriched functional pathways of bacterial proteins present in samples with blood plasma-derived bacterial EV is performed (see FIG. 10C). Gut microbial dysbiosis is reflected in the different expression of these functional pathways or in a taxonomic shift of the bacterial proteins.

In conclusion, the disclosure discloses that circulating bacterial EV are present in a biofluid, are able to induce immune activation and correlate with impaired barrier integrity in patients diagnosed with—but not limited to—IBD, HIV, cancer patients under chemotherapy/pelvic radiotherapy, and cancer patients with chemo/radio therapy-induced intestinal mucositis. This finding together with the documented gut dysbiosis in the patients further discloses that circulating bacterial EV are useful to determine gut microbial dysbiosis.

REFERENCES

1 Stevens B R, Goel R, Seungbum K, et al. Increased human intestinal barrier permeability plasma biomarkers zonulin and FABP2 correlated with plasma LPS and altered gut microbiome in anxiety or depression. *Gut* 2017; 0:1-2.
2 Grander C, Adolph T E, Wieser V, et al. Recovery of ethanol-induced Akkermansia muciniphila depletion ameliorates alcoholic liver disease. *Gut* 2017; 0:1-11.
3 Hänninen A, Toivonen R, Poysti S, et al. Akkermansia muciniphila induces gut microbiota remodelling and controls islet autoimmunity in NOD mice. *Gut* 2017; 0:1-9.
4 Cani P D. Human gut microbiome: hopes, threats and promises. *Gut* 2018; 0:1-10
5 Ellis T N, Kuehn M J. Virulence and Immunomodulatory Roles of Bacterial Outer Membrane Vesicles. *Microbiology and Molecular Biology Reviews: MMBR.* 2010; 74(1):81-94.
6 Wurfel M M, Wright S D. Lipopolysaccharide (LPS) binding protein catalyzes binding of LPS to lipoproteins. *Prog Clin Biol Res.* 1995; 392:287-95.
7 Cohen I R, Norins L C. Natural human antibodies to gram-negative bacteria: immunoglobulins G, A, and M. *Science* 1966; 152(3726): 1257-1259.
8 Yáñez-Mó M, Siljander P R-M, Andreu Z, et al. Biological properties of extracellular vesicles and their physiological functions. *Journal of Extracellular Vesicles* 2015; 4.
9 Wispelwey B, Hansen E J and Scheld W M. Haemophilus influenzae outer membrane vesicle-induced blood-brain barrier permeability during experimental meningitis. *Infect Immun* 1989; 57(8):2559-2562.
10 Tripathi A, Lammers K M, Goldblum S, et al. Identification of human zonulin, a physiological modulator of tight junctions, as prehaptoglobin-2. *Proceedings of the National Academy of Sciences* 2009; 106 (39) 16799-16804.
11 Van Deun J, Mestdagh P, Sormunen R, et al. The impact of disparate isolation methods for extracellular vesicles on downstream RNA profiling. *Journal of Extracellular Vesicles* 2014; 3.
12 Vergauwen G, Dhondt B, Van Deun J, et al. Confounding factors of ultrafiltration and protein analysis in extracellular vesicle research. *Scientific reports* 2017; 7.
13 Sender R, Fuchs S and Milo R. Revised estimates for the number of human and bacteria cells in the body. *PLOS Biology* 2016; 14(8).
14 Hubatsch I, Ragnarsson E G and Artursson P. Determination of drug permeability and prediction of drug absorption in Caco-2 monolayers. *Nat Protoc.* 2007; 2(9):2111-9.
15 Qin J, Li R, Raes J, et al. A human gut microbial gene catalogue established by metagenomic sequencing. *Nature* 2010; 464, 59-65.
16 Pais de Barros J P, Gautier T, Sali W, et al. Quantitative lipopolysaccharide analysis using HPLC/MS/MS and its combination with the limulus amebocyte lysate assay. *J Lipid Res.* 2015; 56(7):1363-9.
17 Neto A G, Hickman R A, Khan A, Nossa C and Pei Z. Chapter 1—The Upper Gastrointestinal Tract—Esophagus and Stomach, The Microbiota in Gastrointestinal Pathophysiology 2017; 1-11,
18 Zitvogel L, Ayyoub M, Routy B and Kroemer G, Microbiome and Anticancer Immunosurveillance. *Cell* 2016; 165(2):276-87.
19 Kuek A, Hazleman B L and Ostör A J. Immune-mediated inflammatory diseases (IMIDs) and biologic therapy: a medical revolution. *Postgrad Med J.* 2007; 83(978):251-60.

The invention claimed is:
1. An in vitro method to determine intestinal barrier permeability and gut microbial dysbiosis in a subject, the method comprising:
  isolating bacterial extracellular vesicles (EV) from a biofluid sample from the subject,
  determining the level of lipopolysaccharide (LPS) and lipoteichoic acid (LTA) activity of the bacterial EV,
  determining the 16S rRNA content of the bacterial EV,
  determining the protein content of the bacterial EV, and
  quantifying a bacterial EV number,
wherein the level of the LPS and LTA activity and bacterial EV number correlate positively with intestinal barrier permeability and wherein the 16S rRNA and protein content correlate with gut microbial dysbiosis in the subject.
2. An in vitro method according to claim 1, wherein the biofluid sample is blood, saliva, urine, cerebrospinal fluid, stool, ascites fluid, sputum, semen, breast milk or sweat.
3. An in vitro method according to claim 1, wherein isolating bacterial EV from the biofluid sample is undertaken by combining size- and density-based separation.
4. An in vitro method according to claim 1, wherein determining LPS and LTA activity is undertaken by a reporter assay.
5. An in vitro method according to claim 4, wherein the reporter assay is the limulus amebocyte lysate assay and/or the Toll-like receptor 4 assay and/or the Toll-like receptor 2 assay.
6. An in vitro method according to claim 1, wherein determining the 16S rRNA content is undertaken by 16S rRNA gene analysis.
7. An in vitro method according to claim 1, wherein determining the protein content is undertaken by mass spectrometry analysis.
8. An in vitro method according to claim 1, wherein quantifying the bacterial EV number is undertaken by flow cytometry analysis, nanoparticle tracking analysis, or immune-electron microscopy.
9. An in vitro method according to claim 1, wherein the subject was previously diagnosed with inflammatory disease including, but not limited to inflammatory bowel disease, HIV, and cancer, wherein the subject has received pelvic radiation therapy, systemic chemotherapy, and/or immunotherapy.
10. An in vitro method according to claim 1, further comprising: monitoring a therapeutic response in the subject.
11. An in vitro method according to claim 10, wherein the therapeutic response is a change of intestinal barrier function and gut microbial dysbiosis.
12. An in vitro method to determine intestinal barrier permeability in a subject, the method comprising:
  isolating bacterial extracellular vesicles (EV) from a biofluid sample from the subject,
  determining the level of LPS activity and LTA-activity of the bacterial EV, and
  quantifying a bacterial EV number,
wherein the level of the LPS and LTA activity and EV bacterial number correlate positively with intestinal barrier permeability in the subject.

13. An in vitro method to determine gut microbial dysbiosis in a subject diagnosed with an inflammatory disease, wherein the subject is being treated for the inflammatory disease by administration of pelvic radiation therapy, systemic chemotherapy, and/or immunotherapy, the method comprising:
  isolating bacterial extracellular vesicles (EV) from a biofluid sample from the subject,
  determining the 16S rRNA content of the bacterial EV,
  determining the protein content of the bacterial EV, and
  monitoring a change of intestinal barrier function and gut microbial dysbiosis in the subject,
wherein the 16S rRNA and protein content correlate with gut microbial dysbiosis in the subject.

14. The in vitro method according to claim 2, wherein isolating bacterial EV from the biofluid sample is undertaken by combining size-based and density-based separation.

15. The in vitro method according to claim 14, wherein the combined size-based and density-based separation comprises size exclusion chromatography and density gradient centrifugation.

16. The in vitro method according to claim 3, wherein the combined size-based and density-based separation comprises size exclusion chromatography and density gradient centrifugation.

17. The in vitro method according to claim 12, wherein the subject has been diagnosed with an inflammatory disease, and wherein the subject is administered pelvic radiation therapy, systemic chemotherapy, and/or immunotherapy.

18. The in vitro method according to claim 17, further comprising:
  monitoring a therapeutic response in the subject,
  wherein the therapeutic response is a change of intestinal barrier function and gut microbial dysbiosis in the subject.

* * * * *